(12) United States Patent
Vallone

(10) Patent No.: US 8,370,175 B2
(45) Date of Patent: Feb. 5, 2013

(54) ICON-BASED HEALTHCARE MANAGEMENT SYSTEM

(76) Inventor: Anthony J. Vallone, Canton, OH (US)

( * ) Notice: Subject to any disclaimer, the term of this patent is extended or adjusted under 35 U.S.C. 154(b) by 1041 days.

(21) Appl. No.: 11/519,036

(22) Filed: Sep. 11, 2006

(65) Prior Publication Data

US 2008/0065412 A1    Mar. 13, 2008

(51) Int. Cl.
*G06Q 50/00* (2006.01)
(52) U.S. Cl. ................................. 705/3; 705/2
(58) Field of Classification Search .................. 705/2, 3, 705/4

See application file for complete search history.

(56) References Cited

U.S. PATENT DOCUMENTS

| | | | |
|---|---|---|---|
| 7,519,541 B2 * | 4/2009 | Fackler et al. ................... | 705/2 |
| 7,831,449 B2 * | 11/2010 | Ying et al. ...................... | 705/3 |
| 2002/0055855 A1 * | 5/2002 | Cule et al. ...................... | 705/2 |
| 2002/0103675 A1 * | 8/2002 | Vanelli ........................... | 705/3 |
| 2002/0156654 A1 * | 10/2002 | Roe et al. ........................ | 705/3 |
| 2002/0184055 A1 * | 12/2002 | Naghavi et al. ................. | 705/2 |
| 2005/0065813 A1 * | 3/2005 | Mishelevich et al. ........... | 705/2 |
| 2005/0283387 A1 * | 12/2005 | Donoghue et al. .............. | 705/3 |
| 2006/0047540 A1 * | 3/2006 | Hutten et al. ................... | 705/4 |

* cited by examiner

*Primary Examiner* — Gerald J. O'Connor
*Assistant Examiner* — Edward Winston, III
(74) *Attorney, Agent, or Firm* — Cooper Legal Group LLC

(57) ABSTRACT

Systems, methodologies, media, and other embodiments associated with an icon-based healthcare patient care system are described. One exemplary system embodiment includes an icon-based healthcare patient care system comprising an association data store that stores association information between a category and at least one icon; and, a patient care logic configured to provide icon-based healthcare information based on selection information received from a user.

30 Claims, 13 Drawing Sheets

ICON-BASED HEALTHCARE MANAGEMENT SYSTEM

BACKGROUND

The generation and maintenance of patient healthcare records can be a time-consuming task. In the healthcare industry, the current emphasis placed on cost containment has resulted in a higher volume of patients being seen during a given period of time.

BRIEF DESCRIPTION OF THE DRAWINGS

The accompanying drawings, which are incorporated in and constitute a part of the specification, illustrate various example systems, methods, and other example embodiments of various aspects of the invention. It will be appreciated that the illustrated element boundaries (e.g., boxes, groups of boxes, or other shapes) in the figures represent one example of the boundaries. One of ordinary skill in the art will appreciate that one element may be designed as multiple elements or that multiple elements may be designed as one element. An element shown as an internal component of another element may be implemented as an external component and vice versa. Furthermore, elements may not be drawn to scale.

DETAILED DESCRIPTION

Figure 1:
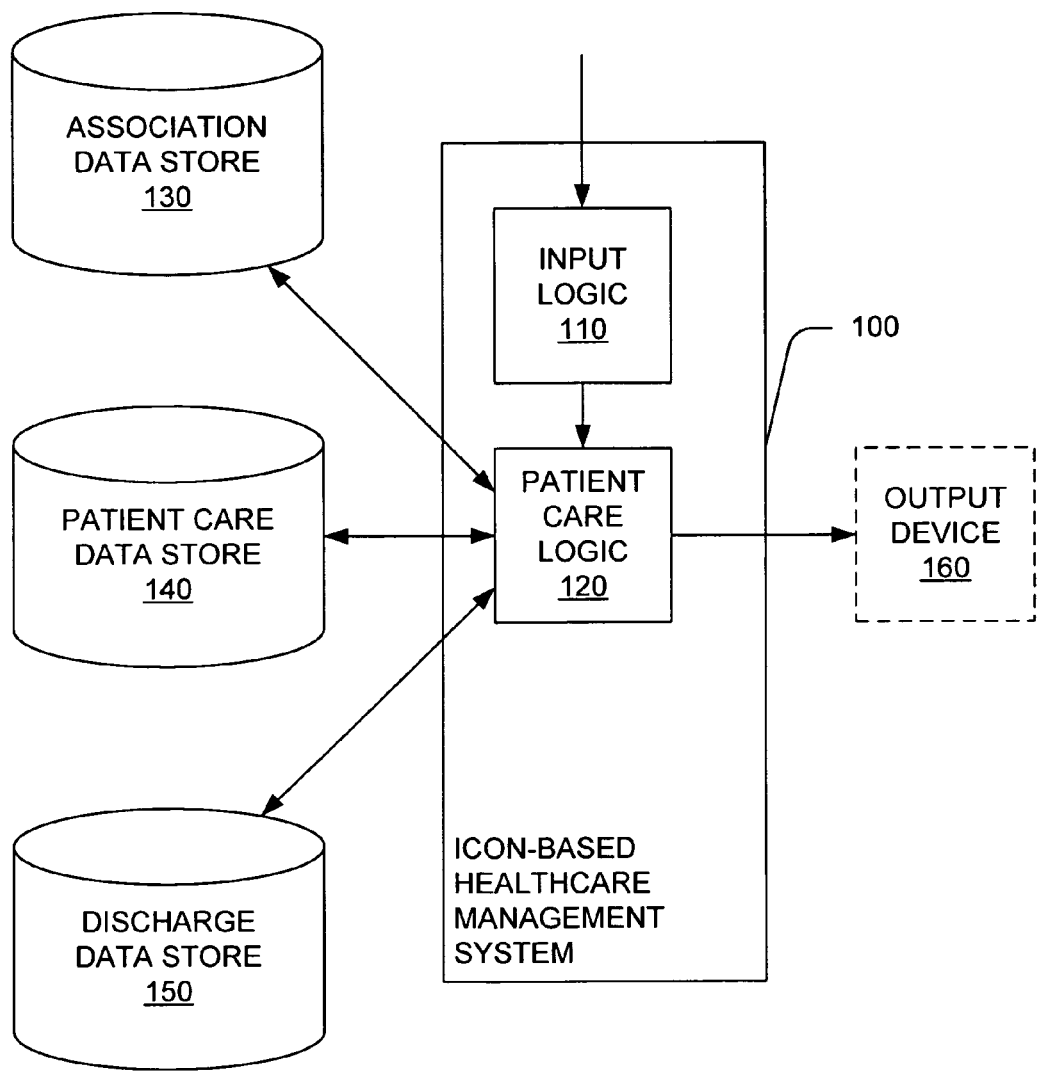
FIG. 1 illustrates an example icon-based healthcare management system.

Example systems, methods, computer-readable media, software and other embodiments are described herein that relate to icon-based healthcare management. In one embodiment, an icon-based healthcare patient care system includes an association data store that stores association information between a category and icon(s). The system further includes a patient care logic configured to provide icon-based healthcare information based on selection information received from a user.

The icon-based healthcare patient care system employs icons to facilitate the entry, retrieval, reviewing (e.g., visually and/or audibly), storage and/or archival of patient healthcare information. For example, a particular icon can represent an object such as a wheelchair and/or when combined with another icon (e.g., a standing figure icon) represents the activity of transferring to/from the wheelchair.

In one embodiment, icons can be language and culture independent. Thus, the icons can have substantially similar meanings to users irrespective of geographic location.

The following includes definitions of selected terms employed herein. The definitions include various examples and/or forms of components that fall within the scope of a term and that may be used for implementation. The examples are not intended to be limiting. Both singular and plural forms of terms may be within the definitions.

As used in this application, the term "computer component" refers to a computer-related entity, either hardware, firmware, software, a combination thereof, or software in execution. For example, a computer component can be, but is not limited to being, a process running on a processor, a processor, an object, an executable, a thread of execution, a program, and a computer. By way of illustration, both an application running on a server and the server can be computer components. One or more computer components can reside within a process and/or thread of execution and a computer component can be localized on one computer and/or distributed between two or more computers.

"Computer-readable medium", as used herein, refers to a medium that participates in directly or indirectly providing signals, instructions and/or data. A computer-readable medium may take forms, including, but not limited to, non-volatile media, volatile media, and transmission media. Non-volatile media may include, for example, optical or magnetic disks and so on. Volatile media may include, for example, semiconductor memories, dynamic memory and the like. Transmission media may include coaxial cables, copper wire, fiber optic cables, and the like. Transmission media can also take the form of electromagnetic radiation, like that generated during radio-wave and infra-red data communications, or take the form of one or more groups of signals. Common forms of a computer-readable medium include, but are not limited to, a floppy disk, a flexible disk, a hard disk, a magnetic tape, other magnetic medium, a CD-ROM, other optical medium, punch cards, paper tape, other physical medium with patterns of holes, a RAM, a ROM, an EPROM, a FLASH-EPROM, or other memory chip or card, a memory stick, a carrier wave/pulse, and other media from which a computer, a processor or other electronic device can read. Signals used to propagate instructions or other software over a network, like the Internet, can be considered a "computer-readable medium."

"Data store", as used herein, refers to a physical and/or logical entity that can store data. A data store may be, for example, a database, a table, a file, a list, a queue, a heap, a memory, a register, and so on. A data store may reside in one logical and/or physical entity and/or may be distributed between two or more logical and/or physical entities.

"Logic", as used herein, includes but is not limited to hardware, firmware, software and/or combinations of each to perform a function(s) or an action(s), and/or to cause a function or action from another logic, method, and/or system. For example, based on a desired application or needs, logic may include a software controlled microprocessor, discrete logic like an application specific integrated circuit (ASIC), an analog circuit, a digital circuit, a programmed logic device, a memory device containing instructions, or the like. Logic may include one or more gates, combinations of gates, or other circuit components. Logic may also be fully embodied as software. Where multiple logical logics are described, it may be possible to incorporate the multiple logical logics into one physical logic. Similarly, where a single logical logic is described, it may be possible to distribute that single logical logic between multiple physical logics.

"Query", as used herein, refers to a semantic construction that facilitates gathering and processing information. A query might be formulated in a database query language like structured query language (SQL) or object query language (OQL). A query might be implemented in computer code (e.g., C#, C++, Javascript) that can be employed to gather information from various data stores and/or information sources.

"Signal", as used herein, includes but is not limited to one or more electrical or optical signals, analog or digital signals, data, one or more computer or processor instructions, messages, a bit or bit stream, or other means that can be received, transmitted and/or detected.

"Software", as used herein, includes but is not limited to, one or more computer or processor instructions that can be read, interpreted, compiled, and/or executed and that cause a computer, processor, or other electronic device to perform functions, actions and/or behave in a desired manner. The instructions may be embodied in various forms like routines, algorithms, modules, methods, threads, and/or programs including separate applications or code from dynamically linked libraries. Software may also be implemented in a variety of executable and/or loadable forms including, but not limited to, a stand-alone program, a function call (local and/or remote), a servelet, an applet, instructions stored in a memory, part of an operating system or other types of executable instructions. It will be appreciated by one of ordinary skill in the art that the form of software may be dependent on, for example, requirements of a desired application, the environment in which it runs, and/or the desires of a designer/programmer or the like. It will also be appreciated that computer-readable and/or executable instructions can be located in one logic and/or distributed between two or more communicating, co-operating, and/or parallel processing logics and thus can be loaded and/or executed in serial, parallel, massively parallel and other manners.

Suitable software for implementing the various components of the example systems and methods described herein include programming languages and tools like Java, Pascal, C#, C++, C, CGI, Perl, SQL, APIs, SDKs, assembly, firmware, microcode, and/or other languages and tools. Software, whether an entire system or a component of a system, may be embodied as an article of manufacture and maintained or provided as part of a computer-readable medium as defined previously. Another form of the software may include signals that transmit program code of the software to a recipient over a network or other communication medium. Thus, in one example, a computer-readable medium has a form of signals that represent the software/firmware as it is downloaded from a web server to a user. In another example, the computer-readable medium has a form of the software/firmware as it is maintained on the web server. Other forms may also be used.

"User", as used herein, includes but is not limited to one or more persons, software, computers or other devices, or combinations of these.

Some portions of the detailed descriptions that follow are presented in terms of algorithms and symbolic representations of operations on data bits within a memory. These algorithmic descriptions and representations are the means used by those skilled in the art to convey the substance of their work to others. An algorithm is here, and generally, conceived to be a sequence of operations that produce a result. The operations may include physical manipulations of physical quantities. Usually, though not necessarily, the physical quantities take the form of electrical or magnetic signals capable of being stored, transferred, combined, compared, and otherwise manipulated in a logic and the like.

It has proven convenient at times, principally for reasons of common usage, to refer to these signals as bits, values, elements, symbols, characters, terms, numbers, or the like. It should be borne in mind, however, that these and similar terms are to be associated with the appropriate physical quantities and are merely convenient labels applied to these quantities. Unless specifically stated otherwise, it is appreciated that throughout the description, terms like processing, computing, calculating, determining, displaying, or the like, refer to actions and processes of a computer system, logic, processor, or similar electronic device that manipulates and transforms data represented as physical (electronic) quantities.

FIG. 1 illustrates an icon-based healthcare management system 100. As used herein, "icon" refers to a graphic symbol and/or word whose form represents and/or suggests its meaning. The system 100 can facilitate the entry, retrieval, reviewing (e.g., visually and/or audibly), storage and/or archival of patient healthcare information. The icon-based healthcare management system 100 can be employed as a component of a desktop computer, a laptop computer, a personal digital assistant and the like.

Traditionally, patient healthcare information has been maintained in text-based handwritten and/or typed notes as currently seen with the advent of computers. Limitations in this system persist including an inordinate amount of user time that is spent in locating, reading and/or comprehending information. In addition, the current system is restricted due to formatting variability of information in addressing visit notes and/or reports.

The icon-based healthcare management system 100 employs icons that represent information that facilitate the entry, retrieval, reviewing (e.g., visually and/or audibly), storage and/or archival of patient healthcare information (e.g., in standardized format(s)). In one example, an icon can represent a stand-alone item (e.g., as a wheelchair for adaptive equipment and/or a bandage for an open wound), a condition (e.g., represented when an enlarged icon foot image for edema in the feet) and/or an activity (e.g., when a shirt is selected to represent dressing the upper body). In addition, stand-alone icons may be combined together (icon sequence) to represent an activity, for example, such as seen when a wheelchair is combined with a standing figure-representing a transfer activity of an individual moving from a wheelchair to a standing position. In one embodiment, icons are generally language and culture independent. That is, the icon will mean the same to a user in the United States and a user in Japan.

The icon-based healthcare patient care system 100 includes an input logic 110 configured to receive information (e.g., selection information, patient information, text notes etc.) from a user. For example, the input logic 110 can receive information from a pointing device (a computer mouse, joy stick, jog wheel and/or touch screen etc.) and/or a computer keyboard.

In one embodiment, the input logic 110 can include a voice recognition engine. For example, the voice recognition engine can be trained on a vocabulary associated with a particular healthcare application, as discussed below.

The icon-based healthcare patient care system 100 further includes a patient care logic 120 configured to provide (e.g., display) icon-based healthcare information based on the information received by the input logic 110. The output of the patient care logic 120 can be provided to an output device 160 such as a display device such as a computer screen, a display of a personal digital assistant and/or an image projector. For example, based on information received from the input logic 110, the patient care logic 120 can display a particular grouping of icons. In one embodiment, the system 100 includes the output device 160.

The patient care logic 120 can retrieve the grouping of icons based upon an identifier, for example, a category of physical therapy activities such as "transfers". The identifier and associated icons can be stored in an association data store 130 that stores association information. For example, the association data store 130 can store an association between a physical therapy category (e.g., transfers) and associated icons (e.g., wheelchair, car, standing etc.).

Additionally, in one embodiment, the association data store 130 can store category specific information. For example, upon selection of two transfer icons, additional information associated with the activity can be requested and/or displayed (e.g., measure entry(ies)). Further, in one example, information can be stored hierarchically in the association data store 130.

In one embodiment, the association data store 130 can further store associated controller information. For example, the association data store 130 can store information associated with controller options associated with a particular physical therapy category.

The icon-based healthcare management system 100 can further store information associated with one or more patients in a patient care data store 140 as discussed in greater detail below.

Exemplary healthcare industries in which the icon-based healthcare patient care system 100 can be employed include physical therapy, occupational therapy, nurse aid, nursing, physicians and/or hospitals. However, those skilled in the art will recognize that the icon-based healthcare patient care system 100 can be employed in any suitable healthcare industry in which patient information is entered, retrieved, reviewed (e.g., visually and/or audibly), stored and/or archived. All such healthcare industries are intended to be encompassed by the hereto appended claims.

In one example, when a pointing device and/or computer keyboard hovers over a particular icon, a textual and/or audible explanation of the icon can be presented. For example, when a user hovers over a wheelchair icon with a pointing device, the text "wheelchair" can be displayed (e.g., for a brief period of time or continuously). Additionally and/or alternatively, the phrase "wheelchair" can be output, for example, via a speaker.

FIGS. 2-7 illustrate a series of exemplary graphical user interfaces that can be employed with the icon-based healthcare patient care system 100. FIGS. 2-7 will be explained with respect to the physical therapy profession.

Figure 2:
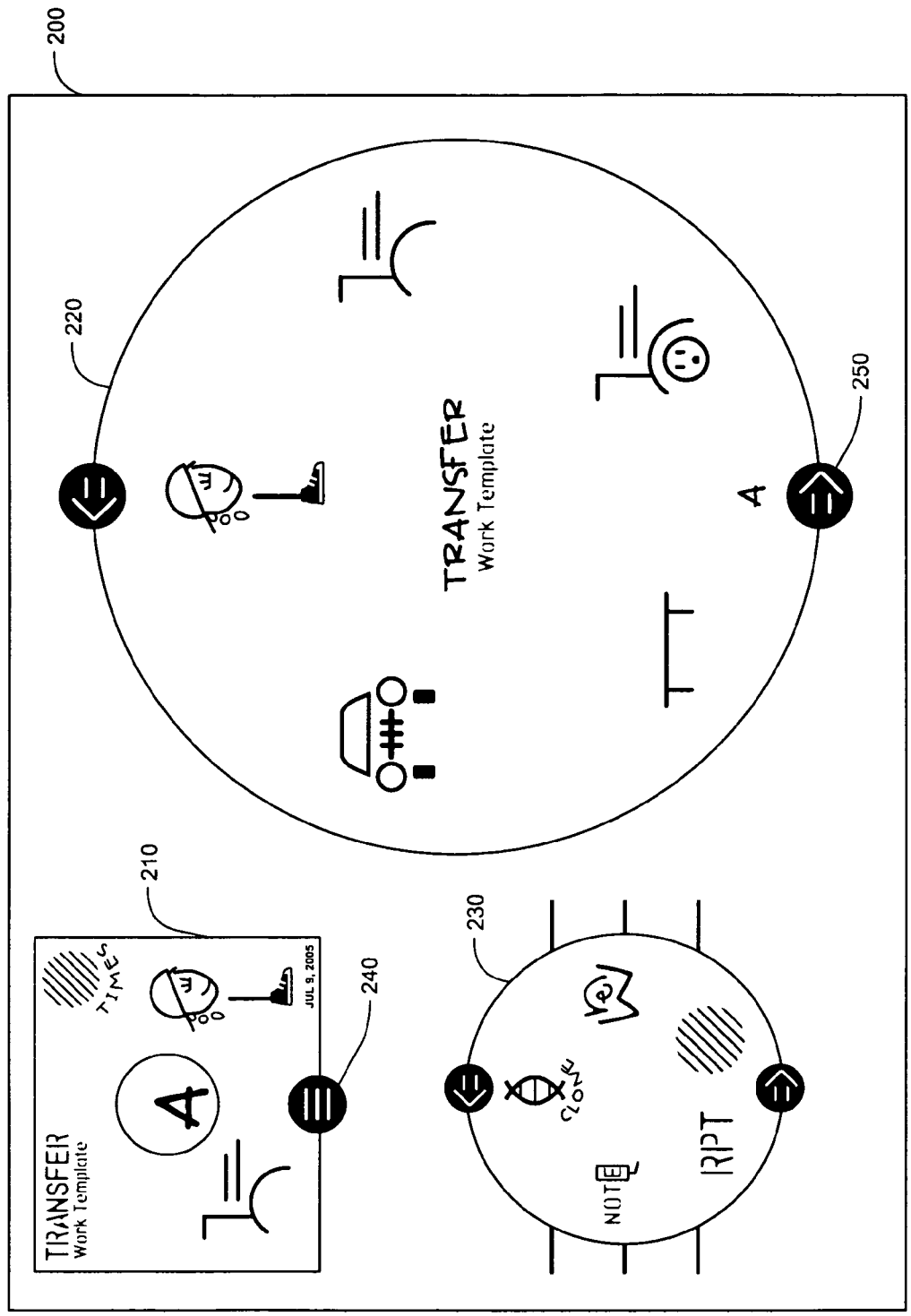
FIG. 2 illustrates an exemplary user interface.

FIG. 2 illustrates an exemplary user interface 200 of a physical therapy application. The user interface 200 includes an activity unit box 210, a category palette 220 and a controller palette 230. The user interface 200 can be generated based on information provided by the icon-based healthcare patient care system 100.

In this example, the physical therapy category "transfers" is illustrated. A particular category can have one or more icons associated with the category. For example, a category and its associated icon(s) can be stored in an association data store 130.

In one embodiment, the patient care logic 120 can retrieve icon(s) associated with a particular category. A user can browse through available categories by selecting a change category button 240. After the user selects the change category button 240, the activity unit box 210 can display a title of the category, the category palette 220 can display icon(s) associated with the category, and the controller palette 230 can display controller icon(s).

Once the category desired by the user is displayed, the user can select a first icon associated with the category from the category palette 220. In one example, the user can browse through available icons by selecting a change palette button 250. Thereafter, the user can select a second icon associated with the category from the category palette 220.

As discussed previously, in response to selection of icon(s), based on information stored in the association data store 130, the patient care logic 120 can retrieve and display additional information associated with the activity.

Additionally, in one example, a user can add text-based variable information in a historical format to a specific icon or an icon sequenced relationships in qualifying an activity or condition For example, if presented icons include a wheelchair and a standing figure, the variable information can include "orthostatic hypotension" when performing this activity ("light head when getting up too fast from a sitting position"). Subsequent visits to this icon relationship will enable the user to add historical information "in one place" as per an option in the resolution or in the continued addressing of an on-going medical condition. The text can be received, for example via a computer keyboard, voice recognition engine and/or a pointing device. In one example, upon selection of a note icon, a user is presented with a graphical representation of a typewriter which the user can employ to enter text.

Figure 3:
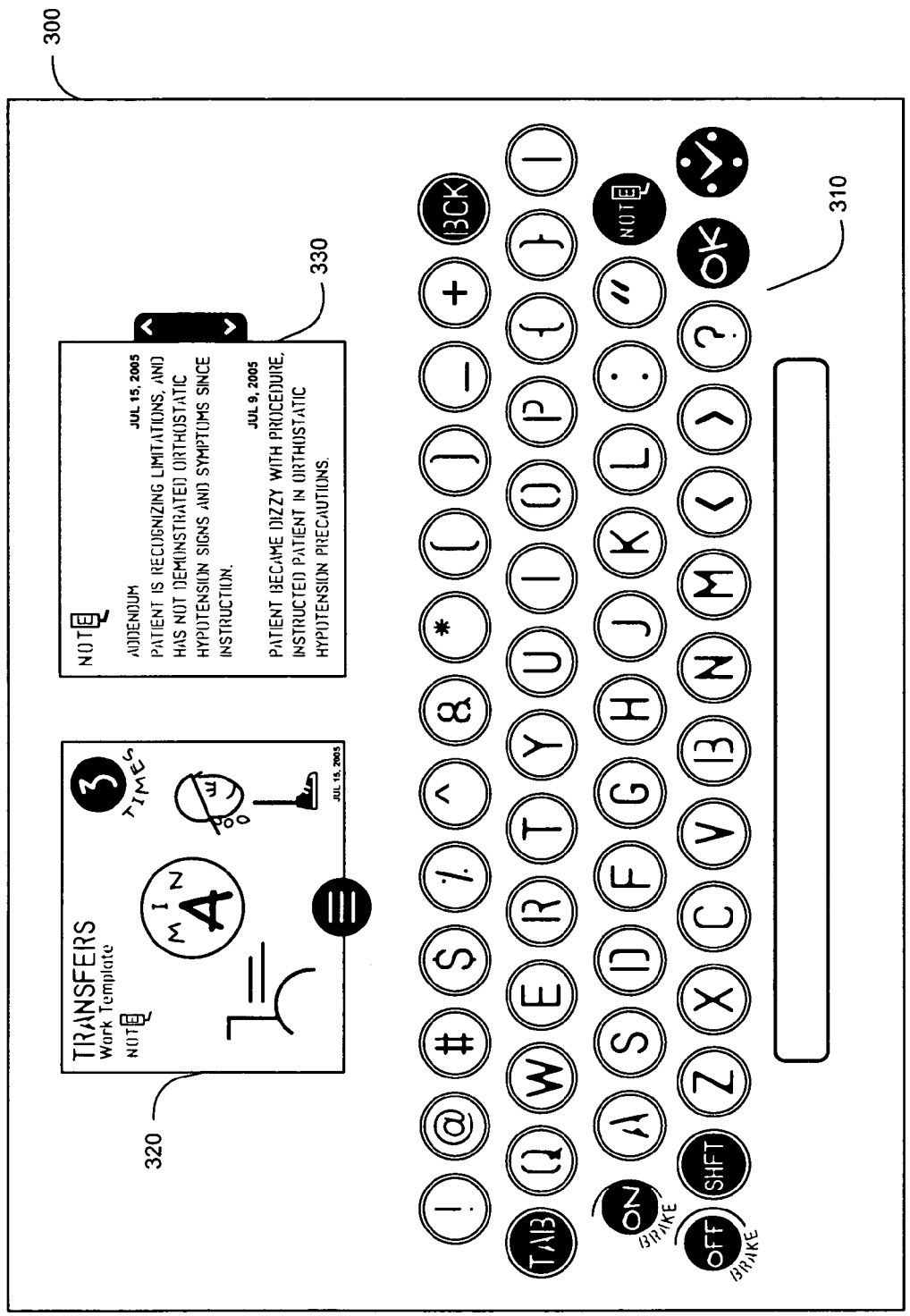
FIG. 3 illustrates an exemplary user interface.

FIG. 3 illustrates an exemplary user interface 300 comprising a graphical representation of a typewriter 310, a unit box 320 and a note box 330. With the user interface 300, a user can enter, retrieve, review (e.g., visually and/or audibly), store and/or archive patient healthcare information (e.g., that can not be addressed in iconic form with a text and/or language based format through the use of a computer touch and/or voice recognition). In the exemplary user interface 300, current and historical text information can be located and accessible in the note box 330 and is specific to the associated unit box 320 (e.g., activity or condition). Information can be received via the graphical representation of a typewriter 310, for example, via a touch screen, voice recognition engine and/or pointing device.

For example, if the icons presented in the unit box 320 include a wheelchair and a standing figure, a user can add descriptive information via the user interface 300 such as "orthostatic hypotension when performing this activity" and/or "light headed when getting up too fast from a sitting position". On subsequent visits to this specific activity, the user can review and/or add information via the note box 330 (e.g., with respect to resolution or continuation of the particular medical condition).

A user can further selected a "RPT" icon from the controller palette 230, for example, for start of care, resumption of care, recertification, discharge, updates and/or adverse event(s) etc.

Figure 4:
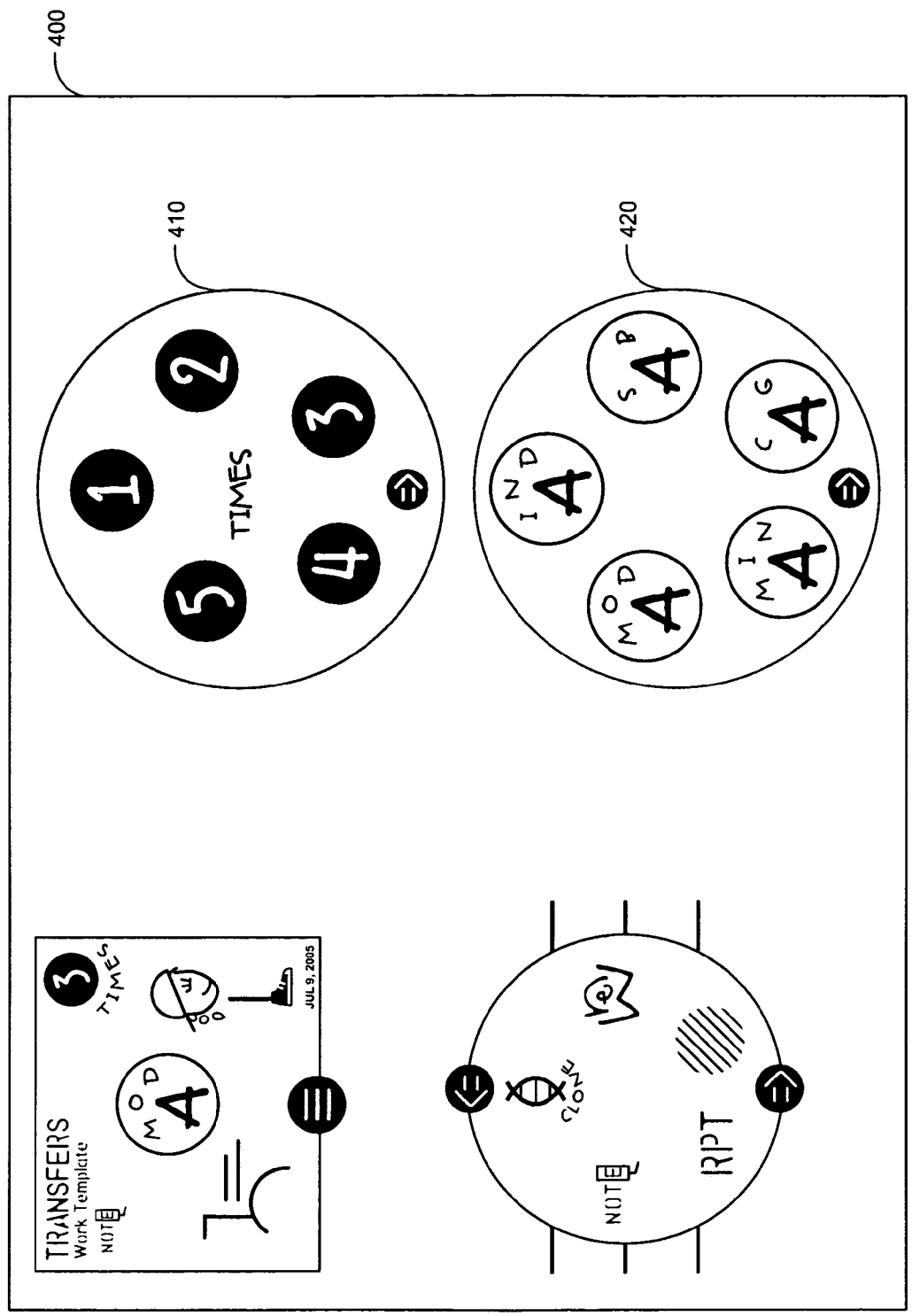
FIG. 4 illustrates another exemplary user interface.

Continuing with this example, FIG. 4 illustrates an exemplary user interface 400 comprising a first measure entry palette 410 associated with the quantity of times that the activity is to be performed. The user interface 400 further includes a second measured entry palette 420 associated with a level of assistance for the activity. For example, transfer from wheel chair to stand three times with moderate assistance.

Once entry of information associated with the activity has been completed, information can be stored in the patient care data store 140. Entry of information can be repeated and stored, as necessary (e.g., clone activity). Patient care information is stored in the patient care data store 140 in a standardized manner thus facilitating retrieval of the patient care information. For example, a user can retrieve and review historical icon-based information such as when transferring from the wheelchair to automobile, over it's duration. In doing so, an advantage gained is in determining if the activity is improving, declining or remaining static. In addition, a "critical pathway" may be developed as per Medicare's specifications in addressing the frequency and/or quality of an activity or condition over a prescribed duration.

Figure 5:
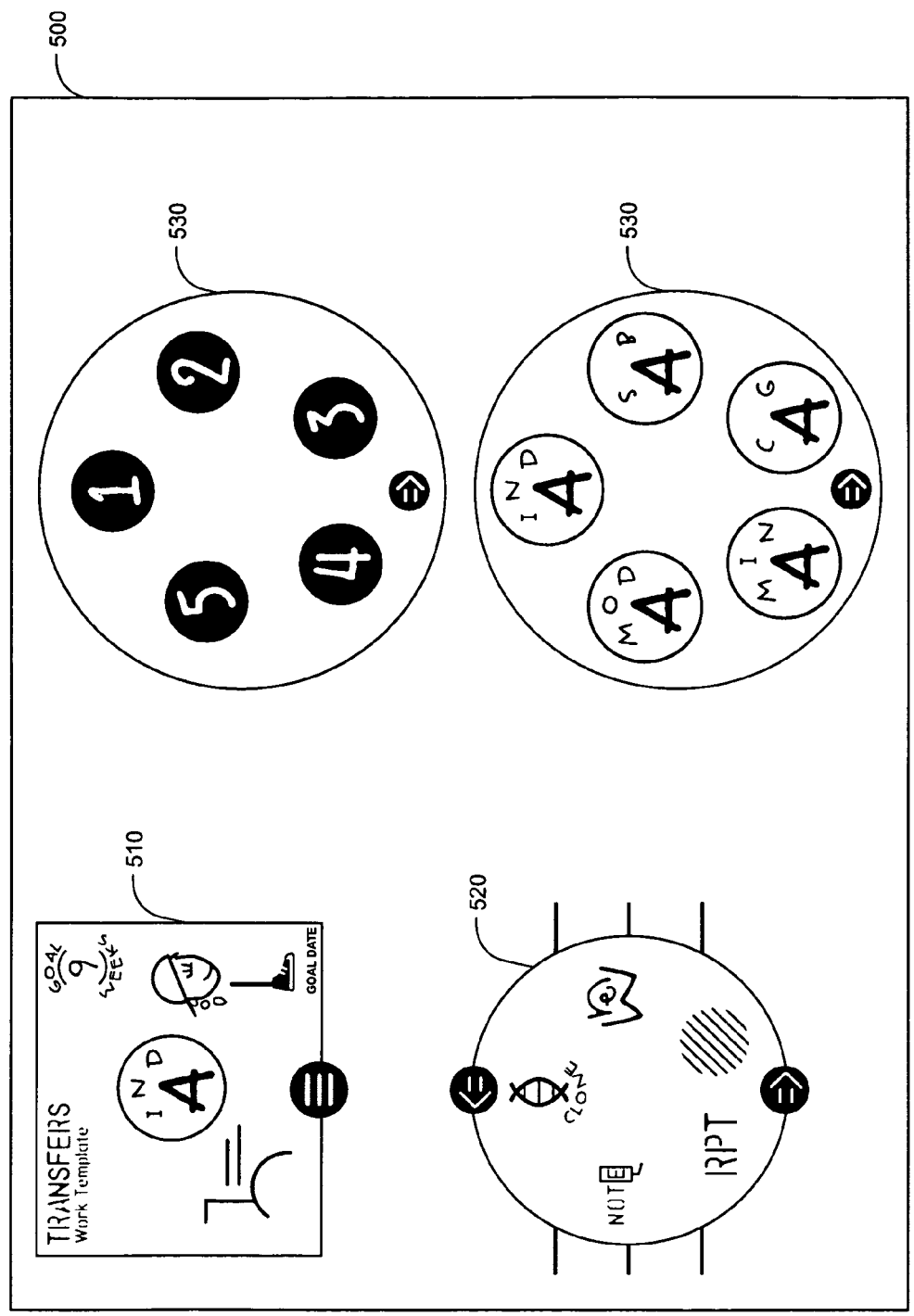
FIG. 5 illustrates another exemplary user interface.

The patient care logic 120 can further retrieve and display goal information for a particular category from the association data store 130. For example, FIG. 5 illustrates an exemplary user interface 500 that includes a goal unit box 510, a controller palette 520, and measure entry palettes 530. In this example, a user can enter information associated with the goal for a particular activity. The goal information can then be stored in the patient care data store 140 and viewed and/or modified at a later time, as discussed below.

Figure 6:
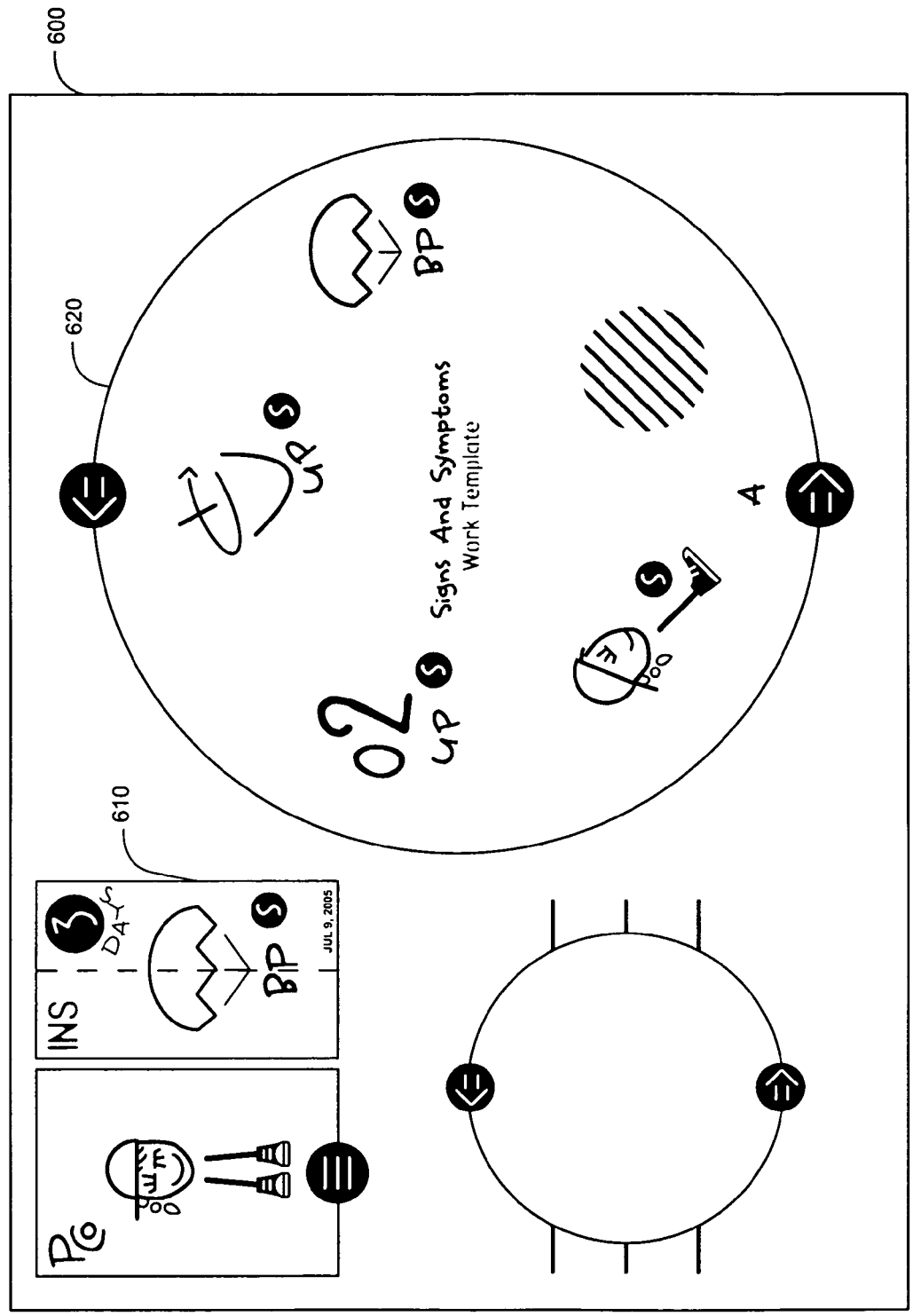
FIG. 6 illustrates another exemplary user interface.

The patient care logic 120 can further retrieve and display or plan of care information for a particular category from the association data store 130. FIG. 6 illustrates an exemplary user interface 600 that includes a plan of care unit box 610 and a plan of care palette 620. The user can select zero, one or more icons from the plan of care palette 620 to include in the plan of care unit box 610. When completed, the user can store the plan of care unit box 610 in the patient care data store 140. The plan of care unit box 610 can be viewed and/or modified by a user on subsequent visit(s).

In the example of FIG. 6, a patient icon and instruct (INS) icon (from previous palette(s) in operational sequence) has been selected along with a parachute/"BP" (blood pressure). To the user, the user interface 600 represents a plan of care (PCo) that the healthcare professional expects the patient to be versed in one or more orthostatic hypotension (decline in blood pressure) signs and symptoms in a given duration through instruction of the medical condition.

With conventional systems, there is no mechanism to "shepard" information from it's creation until it's discharge thereby resulting in a decreased foundation when building subsequent visit notes and reports. With conventional systems, the user is left to their memory and/or time restraints in searching for and interpreting prior notes as current activities or conditions are addressed. In one embodiment, the icon-based health care management system 100 "shepards" information associated with an activity once it is stored in the patient care data store 140, thereby complementing subsequent visit(s), as the activit(ies) information cycles in a closed system requiring it to be addressed by either updating, skipping and/or removing as per user's choice.

In one embodiment, updating an activity during a current visit can be accomplished by "cloning" it's category icon(s) and deleting the previous visit's quantitative selection(s) (e.g., measure entry(ies)). For example, the user can document the number of times a particular transfer occurred along with the current amount of assistance needed to complete the activity.

Figure 7:
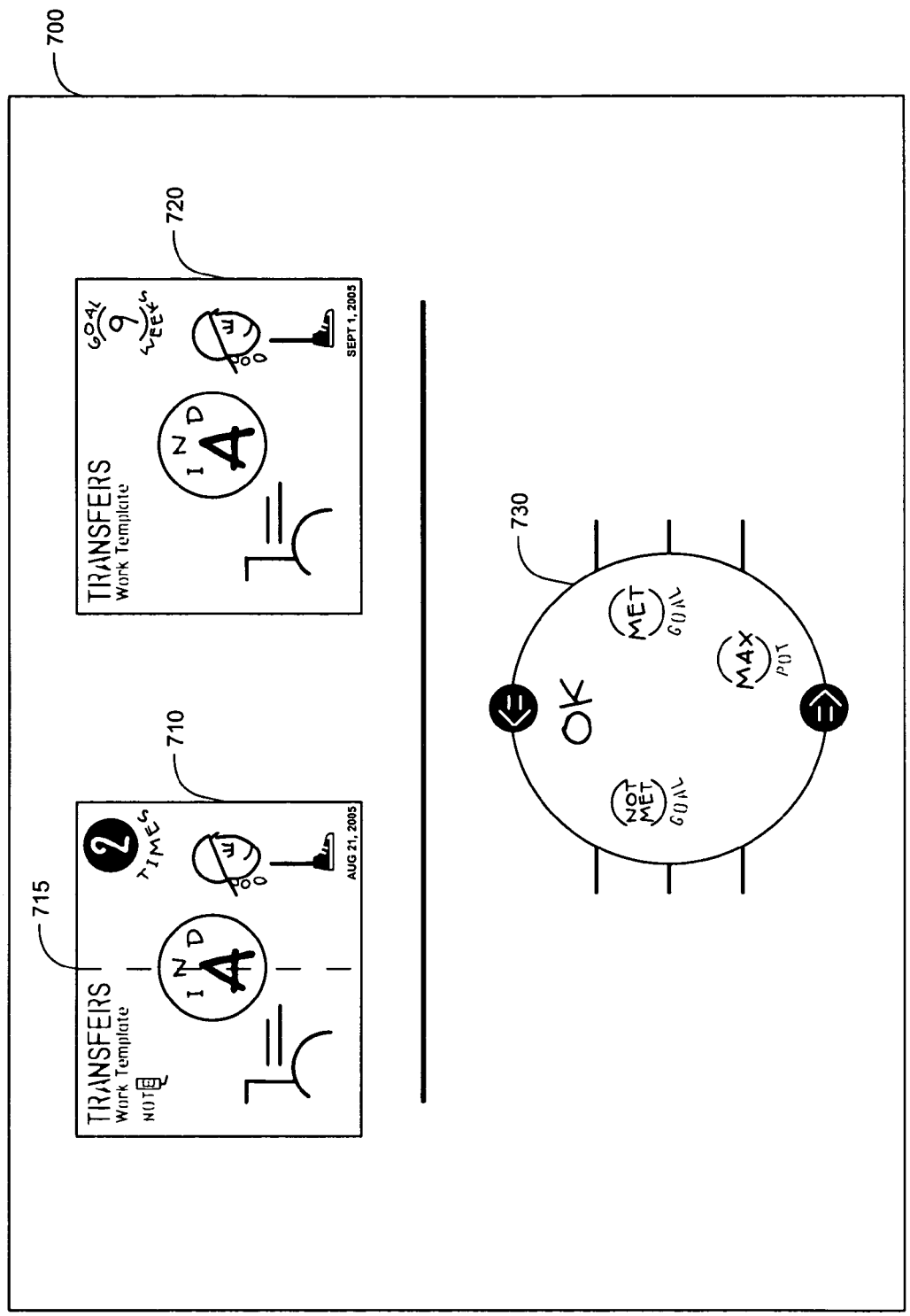
FIG. 7 illustrates another exemplary user interface.

FIG. 7 illustrates an exemplary user interface 700. With the user interface 700, after one or more visits, the user can compare an icon-based visual and/or audio representation of current data 710 with an icon-based visual and/or audio representation of goal data 720. Using a control palette 730, the user can remove the particular activity for the particular patient (e.g., using goal not met, goal met or maximum potential). The removal activity (e.g., goal not met, goal met or maximum potential) can be stored with the goal unit box in the patient care data store 140 and/or a discharge data store 150, for example, for documentation and/or archival purposes. Once the activity has been removed, the activity will no longer be addressed on subsequent visits.

Further, with the system 100, in current and/or subsequent visits, the user can retrieve historical information regarding a particular patient from the patient care data store 140. In one example, once a current unit box 710 is completed, historical information can be accessed allowing the user to visually and/or audibly browse through information regarding the patient's treatment. In one example, the user can select a right-half of an area of the user interface 700 to cycle forward through a history of treatments and a left-half of an area of the user interface 700 to cycle backward through the history of treatments. In the example of FIG. 7, an imaginary line 715 denotes the transition between the left-half and the right-half of the unit box 710. Those skilled in the art will recognize that the imaginary line 715 would not necessarily be depicted on the user interface 700 and is merely included for purposes of explanation of this example.

In one example, activity(ies) that are not removed (e.g., discharged), for example through the user selection option "OK", continue to cycle in the system and be addressed during subsequent visit(s) until removed (e.g., discharged). In this example, upon completion of one or the user options from the controller palette 730, a next activity to be addressed, if any, can be presented to the user via the user interface 700, As noted previously, in one embodiment, the icon-based healthcare management system 100 can include a voice recognition engine. The voice recognition engine can be trained on a vocabulary associated with a particular healthcare application as spoken by a particular user. By using voice recognition, the user can be freed from the physical constraints of using a pointing device and/or computer keyboard to provide information to the icon-based healthcare management system 100. For example, with respect to the physical therapy application discussed previously, the voice recognition engine can be trained to recognize a user's spoken words for the categories "transfers", "bed mobility", "gait", "ambulation" and "activities of daily living" ("ADLs").

Optionally, information stored in the patient care data store 140 and/or the discharge data store 150 can be employed to facilitate billing. For example, information can be retrieved from the patient care data store 140 and/or the discharge data store 150, formatted (e.g., OASIS data specification) and transmitted (e.g., electronically) to an insurer and/or government agency (e.g., Medicare and/or Medicaid).

For example, information stored in the patient care data store 140 and/or discharge data store 150 can be employed in addressing the requirements as noted in Medicare's (and Medicaids) Oasis reports as continued efforts are made in establishing program integrity controls as it relates to healthcare integration in addressing functional improvement and reimbursement.

Example methods may be better appreciated with reference to flow diagrams. While for purposes of simplicity of explanation, the illustrated methodologies are shown and described as a series of blocks, it is to be appreciated that the methodologies are not limited by the order of the blocks, as some blocks can occur in different orders and/or concurrently with other blocks from that shown and described. Moreover, less than all the illustrated blocks may be required to implement an example methodology. Blocks may be combined or separated into multiple components. Furthermore, additional and/or alternative methodologies can employ additional, not illustrated blocks. While the figures illustrate various actions occurring in serial, it is to be appreciated that various actions could occur concurrently, substantially in parallel, and/or at substantially different points in time.

Figure 8:
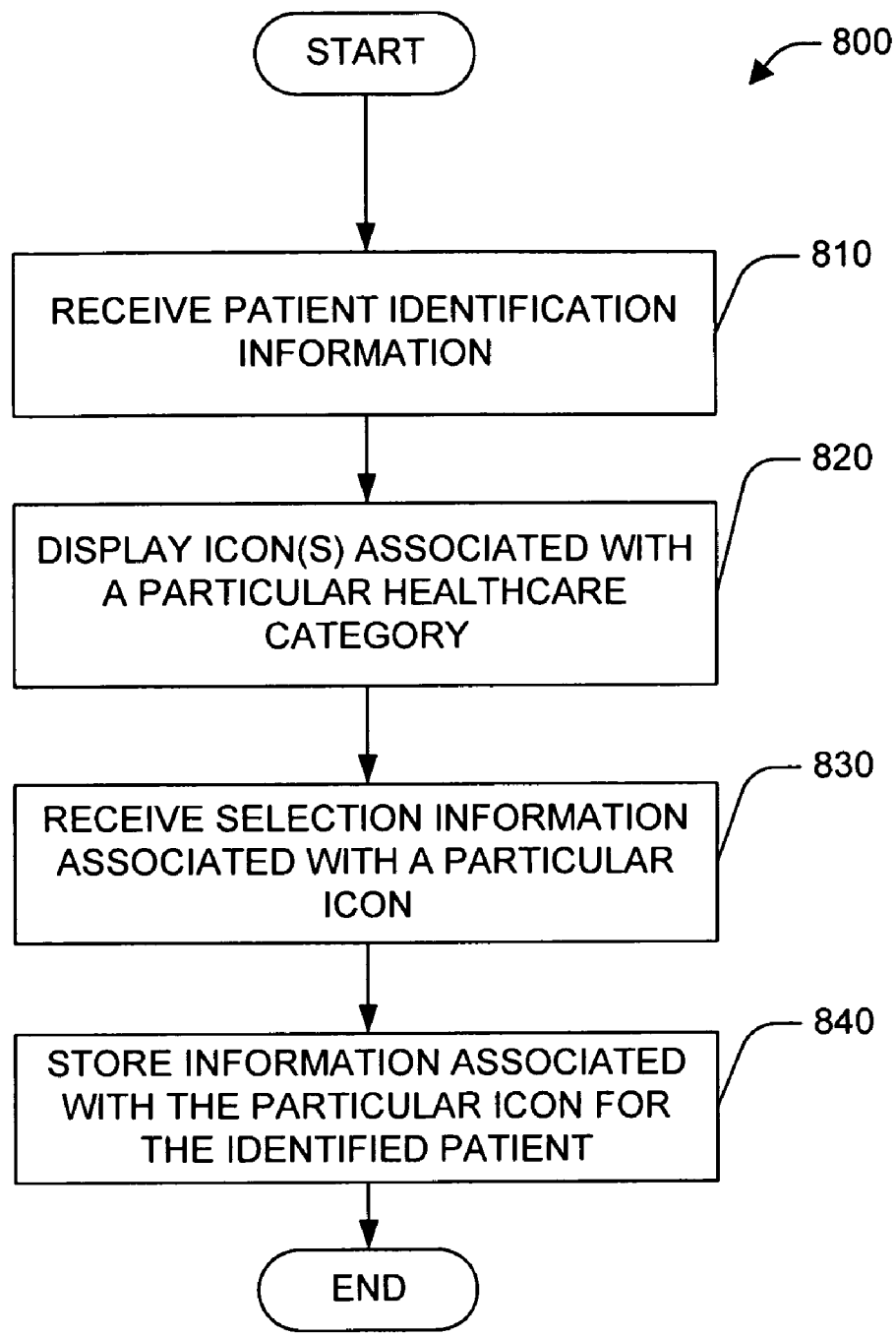
FIG. 8 illustrates an exemplary method for managing patient healthcare information.

Illustrated in FIG. 8 is an example methodology 800 for managing patient healthcare information. The illustrated elements denote "processing blocks" that may be implemented in logic. In one example, the processing blocks may represent executable instructions that cause a computer, processor, and/ or logic device to respond, to perform an action(s), to change states, and/or to make decisions. Thus, the described methodologies can be implemented as processor executable instructions and/or operations provided by a computer-readable medium. In another example, the processing blocks may represent functions and/or actions performed by functionally equivalent circuits such as an analog circuit, a digital signal processor circuit, an application specific integrated circuit (ASIC), or other logic device. The diagram of FIG. 8, as well as the other illustrated diagrams, are not intended to limit the implementation of the described examples. Rather, the diagrams illustrate functional information one skilled in the art could use to design/fabricate circuits, generate software, or use a combination of hardware and software to perform the illustrated processing.

It will be appreciated that electronic and software applications may involve dynamic and flexible processes such that the illustrated blocks can be performed in other sequences different than the one shown and/or blocks may be combined or separated into multiple components. Blocks may also be performed concurrently, substantially in parallel, and/or at substantially different points in time. They may also be implemented using various programming approaches such as machine language, procedural, object oriented and/or artificial intelligence techniques. The foregoing applies to all methodologies described herein.

FIG. 8 illustrates an exemplary method for managing patient healthcare information. At 810, patent identification information is received. In one embodiment, a user can enter (e.g., with a pointing device and/or verbally) a patient's name and/or a patent identifier (e.g., numeric and/or alphanumeric identifier). In one example, a patient can provide biometric information for purposes of identification (e.g., fingerprint, retinas, iris and the like). In another example, a patient can submit a voice sample which can be employed for identification purposes.

Next, at 820, icon(s) associated with a particular healthcare category are displayed to the user. For example, the icon(s) can be retrieved from an association data store 130.

At 830, selection information associated with a particular icon is received. In one embodiment, the selection information is received from a pointing device. In another embodiment, the selection information is received by a verbal command from the user. At 840, information associated with the selected icon for the identified patient is stored (e.g., in a patient care data store 140) and the method 800 ends.

While FIG. 8 illustrates various actions occurring in serial, it is to be appreciated that various actions illustrated in FIG. 8 could occur substantially in parallel. By way of illustration, a first process could receive patient identification information. Similarly, a second process could display icon(s) associated with a particular healthcare category, while a third process could receive selection information associated with a particular icon. While three processes are described, it is to be appreciated that a greater and/or lesser number of processes could be employed and that lightweight processes, regular processes, threads, and other approaches could be employed.

Figure 9:
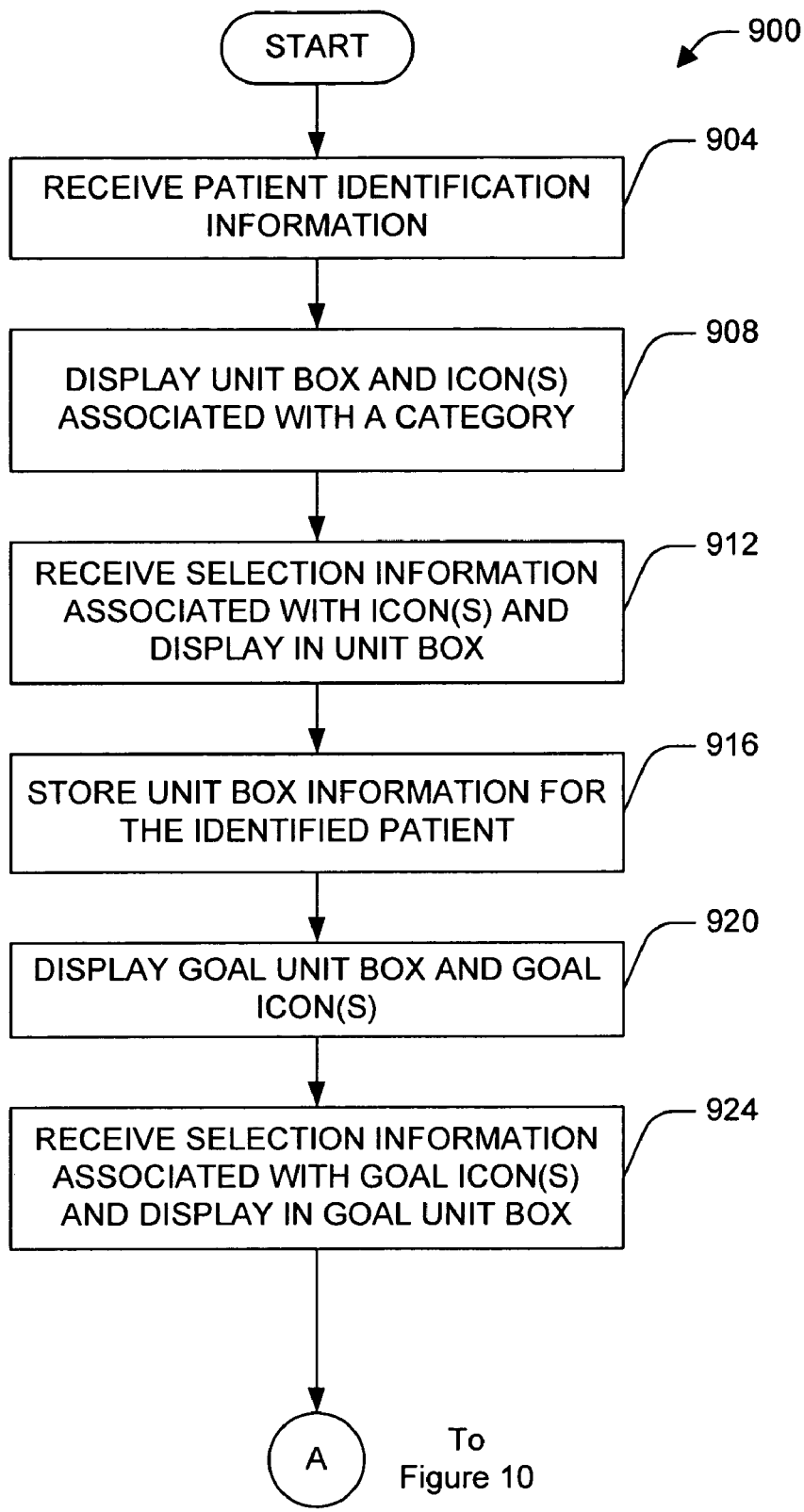
FIG. 9 illustrates a method for managing patient healthcare information.
Figure 10:
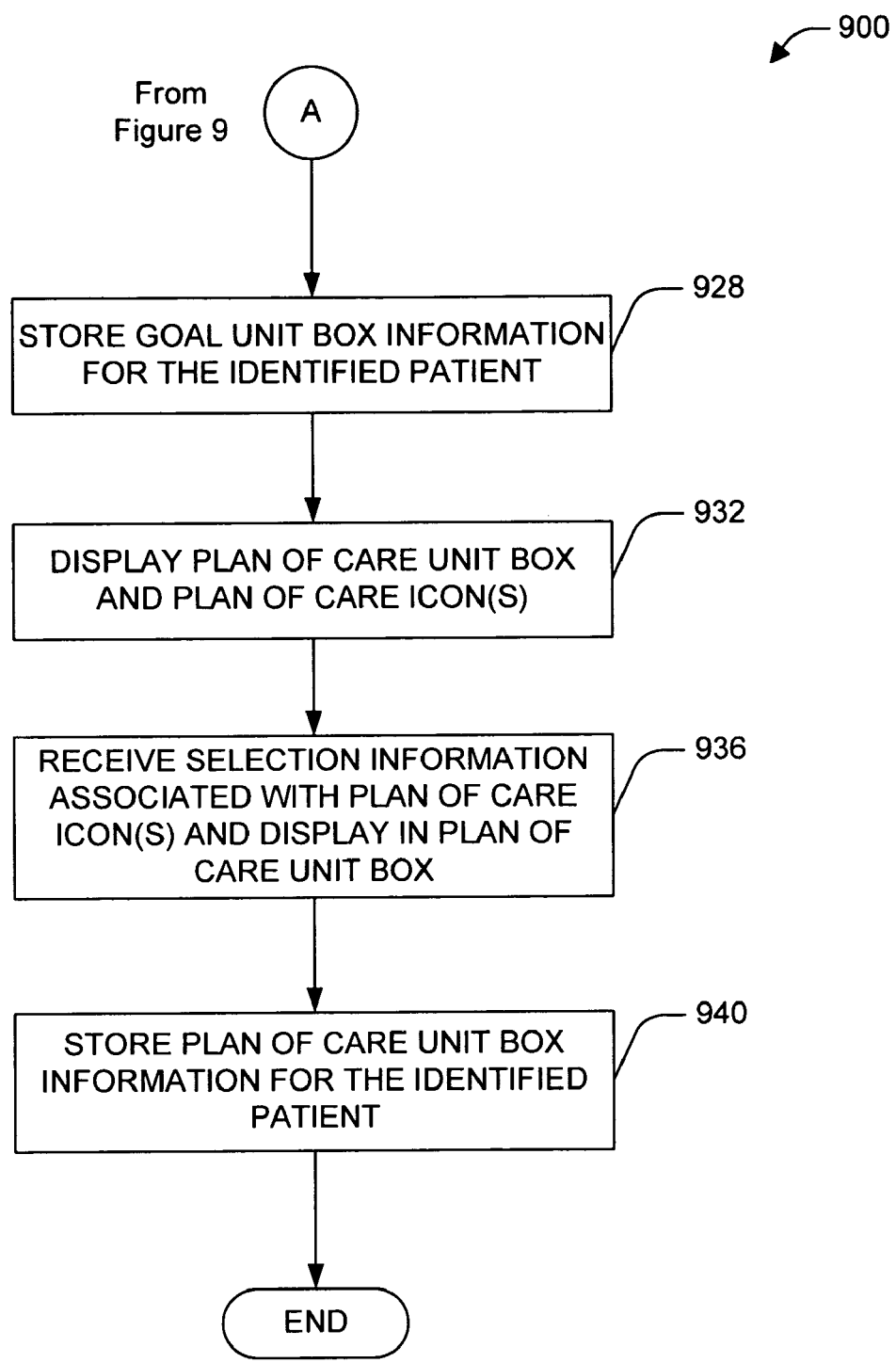
FIG. 10 further illustrates the method of FIG. 9.

FIGS. 9 and 10 illustrate a method 900 for managing patient healthcare information. For example, the method 900 can be employed in a physical therapy setting facilitating identification of activity(ies), goal(s) and a plan of care for a particular patient.

At 904, patient identification information is received. At 908, a unit box and icon(s) associated with a category (e.g., physical therapy category such as "transfers") are displayed. At 912, selection information associated with the icon(s) is received and displayed in the unit box. For example, one or more icons are selected and then displayed in the unit box. Optionally, if appropriate, information associated with measured entry(ies) can further be displayed. Selection information associated with the measured entry(ies) can be received and then displayed in the unit box.

At 916, the unit box information for the identified patient is stored, for example, in a patient care data store 140. At 920, a goal unit box and goal icon(s) are displayed, for example, via the user interface 500 illustrated in FIG. 5.

At 924, selection information associated with the goal icon(s) is received and displayed in the goal unit box. At 928 the goal unit box information for the identified patient is stored, for example, in a patient care data store 140.

At 932, a plan of care unit box and plan of care icon(s) are displayed, for example, via the user interface 600 illustrated in FIG. 6. At 936, selection information associated with the plan of care icon(s) is received and displayed in the plan of care unit box. At 940, the plan of care unit box information for the identified patient is stored for the identified patient, and, the method 900 ends. Those skilled in the art will recognize that action 908 through 940 can be repeated once or more than once to create and store an overall healthcare plan for a particular patient.

Figure 11:
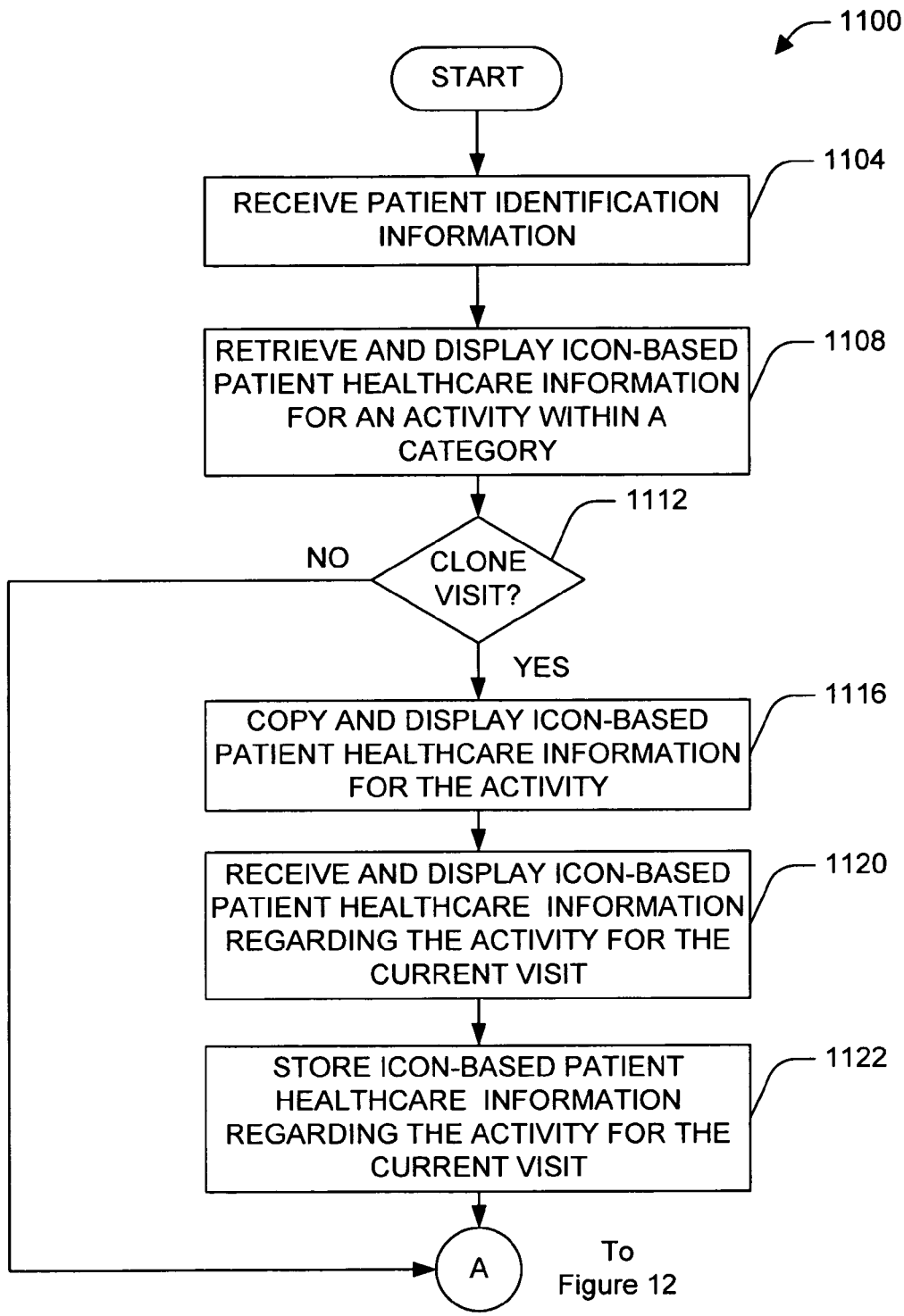
FIG. 11 illustrates a method for managing patient healthcare information.
Figure 12:
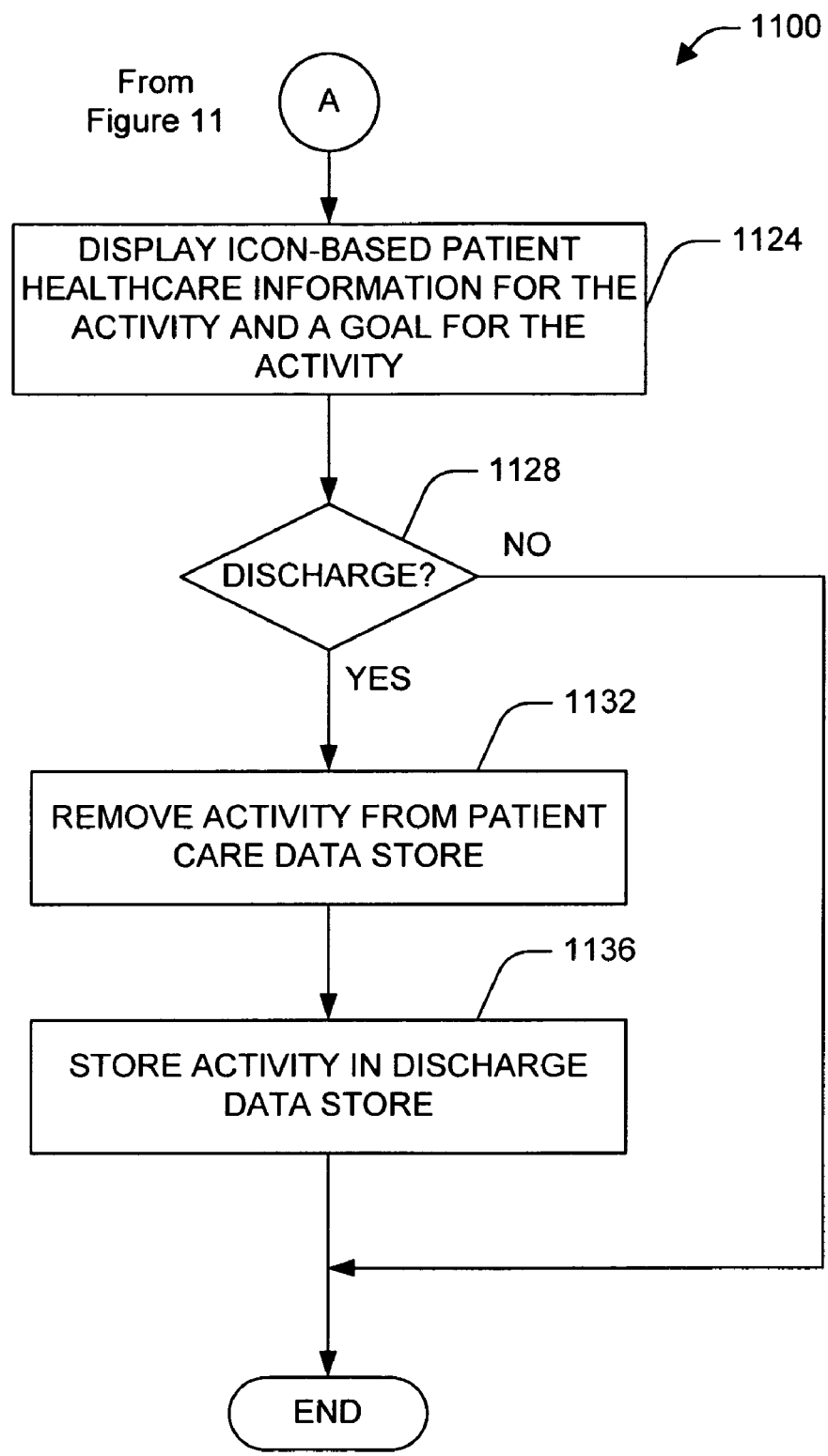
FIG. 12 further illustrates the method of FIG. 11.

FIGS. 11 and 12 illustrate a method 1100 for managing patient healthcare information. The method 1100 can be employed, for example, on subsequent visit(s) of a patient.

At 1104, patient identification information is received. At 1108, icon-based patient healthcare information for an activity within a category is retrieved (e.g., from a patient healthcare store 140) and displayed. At 1112, a determination is made as to whether a clone visit has been selected by the user. If the determination at 1112 is YES, at 1116, at least a portion of the patient healthcare information for the activity is copied and displayed. At 1120, icon-based patient healthcare information is received and displayed for the activity regarding a current visit. At 1122, the icon-based patient healthcare information for the activity for the current visit is stored (e.g., in a patient care data store 140) and the method 1100 continues at 1124. If the determination at 1112 is NO, the method 1100 continues at 1124.

At 1124, icon-based patient healthcare information for the activity (e.g., for the current visit) and goal information for the activity are displayed, for example, side-by-side as illustrated in FIG. 7. At 1128, a determination is made as to whether the activity is to be discharged (e.g., goal met, goal not met or maximum potential).

If the determination at 1128 is NO, the method 1100 ends. If the determination at 1128 is YES, at 1132, the activity is removed, for example, from a patient care data store (e.g., patient care data store 140). At 1136, the activity is stored in a discharge data store (e.g., discharge data store 150).

In one example, methodologies are implemented as processor executable instructions and/or operations stored on a computer-readable medium. Thus, in one example, a computer-readable medium may store processor executable instructions operable to perform a method for managing healthcare information. While the above method is described being stored on a computer-readable medium, it is to be appreciated that other example methods described herein can also be stored on a computer-readable medium.

Figure 13:
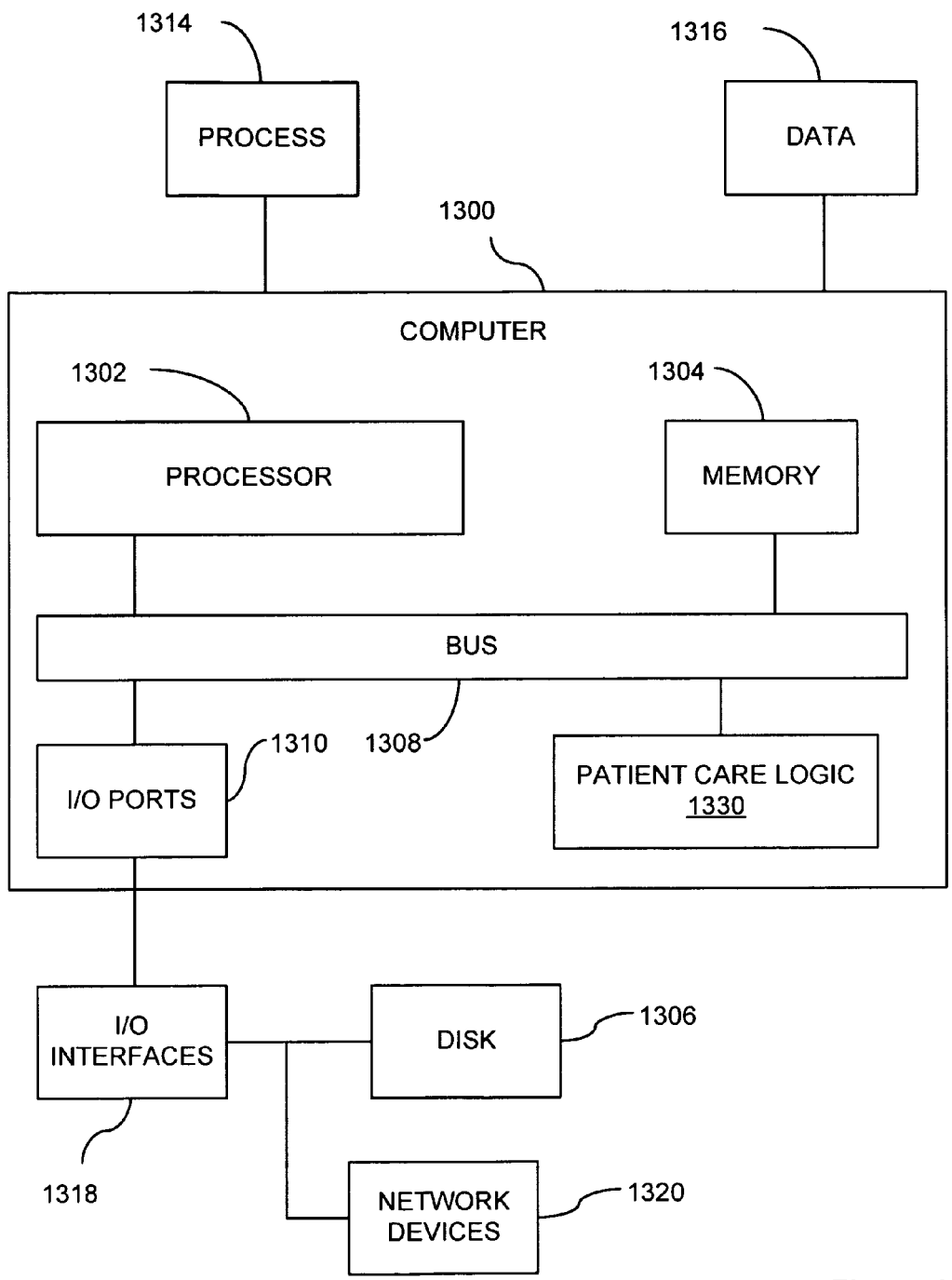
FIG. 13 illustrates an example computing environment in which example systems and methods illustrated herein can operate.

FIG. 13 illustrates an example computing device in which example systems and methods described herein, and equivalents, can operate. The example computing device may be a computer 1300 that includes a processor 1302, a memory 1304, and input/output ports 1310 operably connected by a bus 1308. In one example, the computer 1300 may include a patient care logic 1330 configured to facilitate management of patient healthcare information. The patient care logic 1330 can be implemented similar to the patient care logic 130 described in FIG. 1 and/or the other systems and methods described herein.

The computer 1300 can provide the graphical user interface 200, 300, 400, 500, 600, 700 that is described with reference to FIGS. 2-7, respectively that allow a user to provide icon-based healthcare information.

Generally describing an example configuration of the computer 1300, the processor 1302 can be a variety of various processors including dual microprocessor and other multi-processor architectures. The memory 1304 can include volatile memory and/or non-volatile memory. The non-volatile memory can include, but is not limited to, ROM, PROM, EPROM, EEPROM, and the like. Volatile memory can include, for example, RAM, synchronous RAM (SRAM), dynamic RAM (DRAM), synchronous DRAM (SDRAM), double data rate SDRAM (DDR SDRAM), and direct RAM bus RAM (DRRAM).

A disk 1306 may be operably connected to the computer 1300 via, for example, an input/output interface (e.g., card, device) 1318 and an input/output port 1310. The disk 1306 can include, but is not limited to, devices like a magnetic disk drive, a solid state disk drive, a floppy disk drive, a tape drive, a Zip drive, a flash memory card, and/or a memory stick. Furthermore, the disk 1306 can include optical drives like a CD-ROM, a CD recordable drive (CD-R drive), a CD rewriteable drive (CD-RW drive), and/or a digital video ROM drive (DVD ROM). The memory 1304 can store processes 1314 and/or data 1316, for example. The disk 1306 and/or memory 1304 can store an operating system that controls and allocates resources of the computer 1300.

The bus 1308 can be a single internal bus interconnect architecture and/or other bus or mesh architectures. While a single bus is illustrated, it is to be appreciated that computer 1300 may communicate with various devices, logics, and peripherals using other busses that are not illustrated (e.g., PCIE, SATA, Infiniband, 1394, USB, Ethernet). The bus 1308 can be of a variety of types including, but not limited to, a memory bus or memory controller, a peripheral bus or external bus, a crossbar switch, and/or a local bus. The local bus can be of varieties including, but not limited to, an industrial standard architecture (ISA) bus, a microchannel architecture (MSA) bus, an extended ISA (EISA) bus, a peripheral component interconnect (PCI) bus, a universal serial (USB) bus, and a small computer systems interface (SCSI) bus.

The computer 1300 may interact with input/output devices via i/o interfaces 1318 and input/output ports 1310. Input/output devices can include, but are not limited to, a keyboard, a microphone, a pointing and selection device, cameras, video cards, displays, disk 1306, network devices 1320, and the like. The input/output ports 1310 can include but are not limited to, serial ports, parallel ports, and USB ports.

The computer 1300 can operate in a network environment and thus may be connected to network devices 1320 via the i/o devices 1318, and/or the i/o ports 1310. Through the network devices 1320, the computer 1300 may interact with a network. Through the network, the computer 1300 may be logically connected to remote computers. The networks with which the computer 1300 may interact include, but are not limited to, a local area network (LAN), a wide area network (WAN), and other networks. The network devices 1320 can connect to LAN technologies including, but not limited to, fiber distributed data interface (FDDI), copper distributed data interface (CDDI), Ethernet (IEEE 802.3), token ring (IEEE 802.5), wireless computer communication (IEEE 802.11), Bluetooth (IEEE 802.15.1), and the like. Similarly, the network devices 1320 can connect to WAN technologies including, but not limited to, point to point links, circuit switching networks like integrated services digital networks (ISDN), packet switching networks, and digital subscriber lines (DSL).

While example systems, methods, and so on have been illustrated by describing examples, and while the examples have been described in considerable detail, it is not the intention of the applicants to restrict or in any way limit the scope of the appended claims to such detail. It is, of course, not possible to describe every conceivable combination of components or methodologies for purposes of describing the systems, methods, and so on described herein. Additional advantages and modifications will readily appear to those skilled in the art. Therefore, the invention is not limited to the specific details, the representative apparatus, and illustrative examples shown and described. Thus, this application is intended to embrace alterations, modifications, and variations that fall within the scope of the appended claims. Furthermore, the preceding description is not meant to limit the scope of the invention. Rather, the scope of the invention is to be determined by the appended claims and their equivalents.

To the extent that the term "includes" or "including" is employed in the detailed description or the claims, it is intended to be inclusive in a manner similar to the term "comprising" as that term is interpreted when employed as a transitional word in a claim. Furthermore, to the extent that the term "or" is employed in the detailed description or claims (e.g., A or B) it is intended to mean "A or B or both". When the applicants intend to indicate "only A or B but not both" then the term "only A or B but not both" will be employed. Thus, use of the term "or" herein is the inclusive, and not the exclusive use. See, Bryan A. Garner, A Dictionary of Modern Legal Usage 624 (2d. Ed. 1995).

What is claimed is:

1. A method of presenting a health record of a patient on a device having a processor, a display, and a memory storing an icon set comprising at least one icon, the method comprising: executing on the processor instructions configured to: create in the memory a health record of the patient comprising a set of health conditions of the patient, and, for respective health conditions, a stack of activities having a stack order; upon receiving a request to create an activity for a health condition in the health record of the patient: present upon the device a palette comprising a radial arrangement of activity icons respectively depicting an activity related to the health condition; and upon receiving a selection of an activity icon representing a selected activity, append the selected activity to the stack of activities for the health condition in the health record of the patient; for a selected activity, present upon the display a unit box comprising at least one icon that together represent the health activity; upon receiving a request to cycle forward in the activities, present upon the display a unit box representing a next activity in the stack order of activities associated with the health condition; upon receiving a request to cycle backward in the activities, present upon the display a unit box representing a preceding activity in the stack order of activities associated with the health condition; upon receiving a request to update a selected activity associated with a selected health condition, update the selected activity of the health condition in the health record of the patient stored in the memory; and upon receiving a request to remove a-selected health condition from the health record of the patient, remove the selected health condition in the health record of the patient stored in the memory.

2. The method of claim 1, where the at least one health condition of the health record of the patient is related to at least one of: physical therapy information, nursing information, physician information, occupational therapy information, nurse's aide information, and medical information.

3. The method of claim 1, the method configured to facilitate creation of a visit note of a patient using icons depicting activities associated with a health condition in the health record of the patient.

4. The method of claim 1, comprising: presenting at least one plan of care icon respectively depicting a plan of care of a health condition of the patient; upon receiving a selection of at least one plan of care icon, storing within the health record of the patient in the memory a plan of care unit box representing the plan of care of the health condition for the patient; and presenting on the output device the plan of care unit box comprising at least one plan of care icon that together depicts the plans of care of the health conditions of the patient.

5. The method of claim 1, comprising: presenting at least one goal icon respectively depicting a goal of a health condition of the patient; upon receiving a selection of at least one goal icon, storing within the health record of the patient in the memory goal unit box representing the goal of the health condition for the patient; and presenting on the output device the goal unit box comprising at least one goal icon that together depicts the goal of the health conditions of the patient.

6. The method of claim 1, the health condition stored in the health record of the patient comprising: at least one current health condition that is currently associated with the patient, and at least one historic health condition that is historically associated with the patient.

7. The method of claim 1, comprising: upon receiving a request to update a unit box for a health condition of a patient: storing in the health record of the patient an updated unit box for the health condition of the patient, and presenting on the output device an updated unit box comprising at least one activity icon depicting an activity related to the health condition of the patient.

8. The method of claim 1, comprising: upon receiving from a user textual information associated with at least one activity of a health condition of the patient, attaching the user textual information to a unit box stack representing the activity associated with the health condition; and presenting on the output device the textual information associated with the activity of the health condition.

9. The method of claim 8, receiving the textual information comprising: receiving from the user at least one voice input, and translating the voice input received from the user into the textual information.

10. The method of claim 1, receiving the selection of an activity icon comprising: receiving biometric information associated with the patient, and using the biometric information of the patient, automatically selecting at least one icon associated with the activity of the health condition of the patient.

11. The method of claim 1, present the icons of the icon set upon the output device comprising: presenting the icons of the icon set using a projector.

12. The method of claim 1, an updated health condition comprising a health condition updated from a source health condition and including updated biometric information of the patient.

13. The method of claim 1, the stack comprising unit boxes representing an aspect of the health record of the patient selected from an aspect set comprising: the health conditions of the patient; the activities associated with at least one health condition of the patient; a plan of care for at least one health condition of the patient; and a goal of at least one health condition of the patient.

14. The method of claim 1, the instructions further configured to, upon receiving a request to access a second health condition in the health record of the patient, present upon the display a unit box representing a health activity for the second health condition.

15. The method of claim 1, the health condition stored in the health record of the patient comprising: at least one current activity that is associated with a health condition in the health record of the patient, and at least one historic activity that is associated with a health condition in the health record of the patient.

16. A non-transitory computer-readable storage device comprising instructions that, when executed on a processor of a device having a processor, a display, and a memory storing an icon set comprising at least one icon, cause the device to present a health record of a patient by: creating in the memory a health record of the patient comprising a set of health conditions of the patient, and, for respective health conditions, a stack of activities having a stack order; upon receiving a request to create an activity for a health condition in the health record of the patient: presenting upon the device a palette comprising a radial arrangement of activity icons respectively depicting an activity related to the health condition; and upon receiving a selection of an activity icon representing a selected activity, appending the selected activity to the stack of activities for the health condition in the health record of the patient; for a selected activity, presenting upon the display a unit box comprising at least one icon that together represent the health activity; upon receiving a request to cycle forward in the activities, presenting upon the display a unit box representing a next activity in the stack order of activities associated with the health condition; upon receiving a request to cycle backward in the activities, presenting upon the display a unit box representing a preceding activity in the stack order of activities associated with the health condition; upon receiving a request to update a selected activity associated with a selected health condition, updating the selected activity of the health condition in the health record of the patient stored in the memory; and upon receiving a request to remove a selected health condition from the health record of the patient, removing the selected health condition in the health record of the patient stored in the memory.

17. A method of presenting a health record of a patient on a device having a processor, a display, and a memory storing an icon set comprising at least one icon, the method comprising: executing on the processor instructions configured to: create in the memory a health record of the patient comprising a set of health conditions, respective health conditions respectively having a plan of care and comprising a stack of unit boxes representing: a goal of the health condition, and at least one activity involving the patient and related to the plan of care for the health condition; upon detecting an instance of an activity involving the patient for a health condition in the health record of the patient: append to the set of unit boxes in the health record of the individual a new unit box representing the instance of the activity; determine whether the activity has been discharged according to the goal of the health condition; and upon identifying an activity to be discharged, remove the unit box for the activity from the stack; upon receiving a request to present the health record for a health condition of the individual: generate a stack comprising, among the unit boxes associated with the plan of care of the health condition in the health record of the individual, the unit boxes that have not been discharged; select a current unit box in the stack; and for the current unit box, present upon the display at least one icon that together represent the unit box; and upon receiving a request to present discharged activities in the plan of care for a health condition, present upon the display a stack of unit boxes representing the discharged activities associated with the plan of care.

18. The method of claim 17, where the at least one health condition of the health record of the patient is related to at least one of: physical therapy information, nursing information, physician information, occupational therapy information, nurse's aide information, and medical information.

19. The method of claim 17, the method configured to facilitate creation of a visit note of a patient using icons depicting activities associated with a health condition in the health record of the patient.

20. The method of claim 17, the health condition stored in the health record of the patient comprising: at least one current health condition that is currently associated with the patient, and at least one historic health condition that is historically associated with the patient.

21. The method of claim 17, the instructions further configured to, upon receiving a request to update a unit box for a health condition of a patient: store in the health record of the patient an updated unit box for the health condition of the patient, and present on the output device an updated unit box comprising at least one activity icon depicting an activity related to the health condition of the patient.

22. The method of claim 17, the instructions further configured to: upon receiving from a user textual information associated with at least one activity of a health condition of the patient, attach the user textual information to a unit box stack representing the activity associated with the health condition; and present on the output device the textual information associated with the activity of the health condition.

23. The method of claim 22, receiving the textual information comprising: receiving from the user at least one voice input, and translating the voice input received from the user into the textual information.

24. The method of claim 17, receiving the selection of an activity icon comprising: receiving biometric information associated with the patient, and using the biometric information of the patient, automatically selecting at least one icon associated with the activity of the health condition of the patient.

25. The method of claim 17, present the icons of the icon set upon the output device comprising: presenting the icons of the icon set using a projector.

26. The method of claim 17, an updated health condition comprising a health condition updated from a source health condition and including updated biometric information of the patient.

27. The method of claim 17, the stack comprising unit boxes representing an aspect of the health record of the patient selected from an aspect set comprising: the health conditions of the patient; the activities associated with at least one health condition of the patient; a plan of care for at least one health condition of the patient; a goal of at least one health condition of the patient.

28. The method of claim 17, the instructions further configured to, upon receiving a request to access a second health condition in the health record of the patient, present upon the display a unit box representing a health activity for the second health condition.

29. The method of claim 17, the health condition stored in the health record of the patient comprising: at least one current activity that is associated with a health condition in the health record of the patient, and at least one historic activity that is associated with a health condition in the health record of the patient.

30. A non-transitory computer-readable storage medium comprising instructions that, when executed on a processor of a device having a processor, a display, and a memory storing an icon set comprising at least one icon, cause the device to present a health record of a patient by: creating in the memory a health record of the patient comprising a set of health conditions, respective health conditions respectively having a plan of care and comprising a stack of unit boxes representing: a goal of the health condition, and at least one activity involving the patient and related to the plan of care for the health condition; upon detecting an instance of an activity involving the patient for a health condition in the health record of the patient: appending to the set of unit boxes in the health record of the individual a new unit box representing the instance of the activity; determining whether the activity has been discharged according to the goal of the health condition; and upon identifying an activity to be discharged, removing the unit box for the activity from the stack; upon receiving a request to present the health record for a health condition of the individual: generating a stack comprising, among the unit boxes associated with the plan of care of the health condition in the health record of the individual, the unit boxes that have not been discharged; selecting a current unit box in the stack; and for the current unit box, presenting upon the display at least one icon that together represent the unit box; and upon receiving a request to present discharged activities in the plan of care for a health condition, presenting upon the display a stack of unit boxes representing the discharged activities associated with the plan of care.

* * * * *